(12) United States Patent
Tougasaki (10) Patent No.: US 10,945,619 B2
(45) Date of Patent: Mar. 16, 2021

(54) MEASUREMENT APPARATUS, MEASUREMENT METHOD, AND ELECTRONIC DEVICE PROVIDED WITH MEASUREMENT APPARATUS (71) Applicant: KYOCERA Corporation, Kyoto (JP)

(72) Inventor: Tomoyuki Tougasaki, Yokohama (JP)

(73) Assignee: KYOCERA Corporation, Kyoto (JP)

(*) Notice: Subject to any disclaimer, the term of this patent is extended or adjusted under 35 U.S.C. 154(b) by 510 days.

(21) Appl. No.: 15/318,935

(22) PCT Filed: Jun. 26, 2015

(86) PCT No.: PCT/JP2015/003233
§ 371 (c)(1),
(2) Date: Dec. 14, 2016

(87) PCT Pub. No.: WO2015/198611
PCT Pub. Date: Dec. 30, 2015

(65) Prior Publication Data
US 2017/0127954 A1 May 11, 2017

(30) Foreign Application Priority Data
Jun. 26, 2014 (JP) .............................. JP2014-131734

(51) Int. Cl.
A61B 5/02 (2006.01)
A61B 5/026 (2006.01)
(Continued)

(52) U.S. Cl.
CPC .......... A61B 5/0261 (2013.01); A61B 5/0004 (2013.01); A61B 5/6826 (2013.01);
(Continued)

(58) Field of Classification Search
CPC ... A61B 5/0261; A61B 5/7455; A61B 5/0004; A61B 5/6898; A61B 5/6843;
(Continued)

(56) References Cited

U.S. PATENT DOCUMENTS 8,750,953 B2* 6/2014 Ochs .................. A61B 5/14551
600/323
2008/0112885 A1* 5/2008 Okunev ............... A61B 5/0022
424/9.1
2014/0266776 A1* 9/2014 Miller ................ A61B 5/14865
340/870.01

FOREIGN PATENT DOCUMENTS

JP S54-081691 A 6/1979
JP S59-166853 A 9/1984
(Continued)

OTHER PUBLICATIONS

International Search Report issued in PCT/JP2015/003233; dated Sep. 15, 2015.
(Continued)

Primary Examiner — Rex R Holmes
(74) Attorney, Agent, or Firm — Studebaker & Brackett PC (57) ABSTRACT Provided are a measurement apparatus, a measurement method, and an electronic device provided with a measurement apparatus that can improve the measurement accuracy of biological information. A measurement apparatus includes a measurement unit that measures biological information and a controller that performs control to suspend measurement by the measurement unit when starting predetermined processing during measurement by the measurement unit.

6 Claims, 6 Drawing Sheets (51) Int. Cl.
*H04M 1/725* (2021.01)
*A61B 5/00* (2006.01)

(52) U.S. Cl.
CPC .......... *A61B 5/6843* (2013.01); *A61B 5/6898* (2013.01); *A61B 5/742* (2013.01); *A61B 5/7455* (2013.01); *H04M 1/72522* (2013.01); *H04M 1/72552* (2013.01); *H04M 2250/12* (2013.01)

(58) Field of Classification Search
CPC .. A61B 5/6826; A61B 5/742; H04M 1/72522; H04M 2250/12; H04M 1/72552
See application file for complete search history.

(56) References Cited

FOREIGN PATENT DOCUMENTS

| | | |
|---|---|---|
| JP | H03-021208 Y2 | 5/1991 |
| JP | 2000-350704 A | 12/2000 |
| JP | 2003-058359 A | 2/2003 |
| JP | 2007-151941 A | 6/2007 |
| JP | 2007-319246 A | 12/2007 |
| JP | 2009-066203 A | 4/2009 |
| JP | 2013-186115 A | 9/2013 |
| JP | 2014-14516 A | 1/2014 |

OTHER PUBLICATIONS

Written Opinion issued in PCT/JP2015/003233; dated Sep. 15, 2015; with English language Concise Explanation.
JP Office Action dated Nov. 7, 2017, from corresponding JP Appl No. 2014-131734, with English statement of relevance, 5 pages.

\* cited by examiner

MEASUREMENT APPARATUS, MEASUREMENT METHOD, AND ELECTRONIC DEVICE PROVIDED WITH MEASUREMENT APPARATUS

CROSS-REFERENCE TO RELATED APPLICATION

This application claims priority to and the benefit of Japanese Patent Application No. 2014-131734 filed Jun. 26, 2014, the entire contents of which are incorporated herein by reference.

TECHNICAL FIELD

This disclosure relates to a measurement apparatus, a measurement method, and an electronic device provided with a measurement apparatus.

BACKGROUND

An example of an existing measurement apparatus measures biological information by acquiring biological output information from a test site, such as a fingertip of a subject (user). For example, a blood flow measurement apparatus that measures blood flow as the biological information irradiates a fingertip with laser light and measures the blood flow based on scattered light from the blood flow in a capillary at the fingertip.

SUMMARY

A measurement apparatus according to this disclosure includes:
a measurement unit configured to measure biological information; and
a controller configured to perform control to suspend measurement by the measurement unit when starting predetermined processing during measurement by the measurement unit.

A measurement apparatus according to this disclosure includes:
a measurement unit configured to measure biological information;
a vibration unit configured to generate vibration; and
a controller configured to perform control to prevent the vibration unit from generating vibration while continuing measurement by the measurement unit when starting predetermined processing during measurement by the measurement unit.

A measurement apparatus according to this disclosure includes:
a measurement unit configured to measure biological information; and
a controller configured to perform control, when starting predetermined processing during measurement by the measurement unit, to determine whether to output a result of the measurement in accordance with the measurement made by the measurement unit up until the predetermined processing starts.

An example of a measurement method according to this disclosure includes:
measuring biological information; and
performing control to suspend measurement in the measuring step when predetermined processing is started during measurement in the measuring step.

Another measurement method according to this disclosure includes:
measuring biological information;
generating vibration; and
performing control to prevent generation of vibration in the generating step while continuing measurement in the measuring step when predetermined processing is started during measurement in the measuring step.

Another measurement method according to this disclosure includes:
measuring biological information; and
performing control, when predetermined processing is started during measurement in the measuring step, to determine whether to output a result of the measurement in accordance with the measurement made in the measuring step up until the predetermined processing is started.

BRIEF DESCRIPTION OF THE DRAWINGS

In the accompanying drawings.

DETAILED DESCRIPTION

The following describes embodiments in detail with reference to the drawings.

Embodiment 1

The state of the capillaries at the fingertip, however, changes depending on the contact state with the measurement apparatus. Specifically, blood flow cannot be measured accurately when the pressure on the measurement apparatus from the fingertip is stronger or weaker than a suitable range. Accordingly, in order to measure the biological information accurately, the user needs to contact the test site to the measurement apparatus appropriately. Therefore, means for stabilizing the contact state has been used, such as using a securing mechanism to secure the test site, or securing the contact state between the fingertip and the measurement apparatus by taping or the like.

When a biological information measurement apparatus is mounted in an electronic device, such as a mobile phone, then an operation particular to the electronic device, such as an incoming phone call, may occur during measurement of the biological information. In this way, if other processing interrupts while the measurement apparatus is measuring the biological information, there is a risk that the accuracy of the biological information being measured will worsen for a reason such as the measurement of biological information being impaired, for example by the test site moving upon the user reacting to the interruption.

It would therefore be helpful to provide a measurement apparatus, a measurement method, and an electronic device provided with a measurement apparatus that can improve the measurement accuracy of biological information.

According to this disclosure, it is possible to provide a measurement apparatus, a measurement method, and an electronic device provided with a measurement apparatus that can improve the measurement accuracy of biological information.

Figure 1:
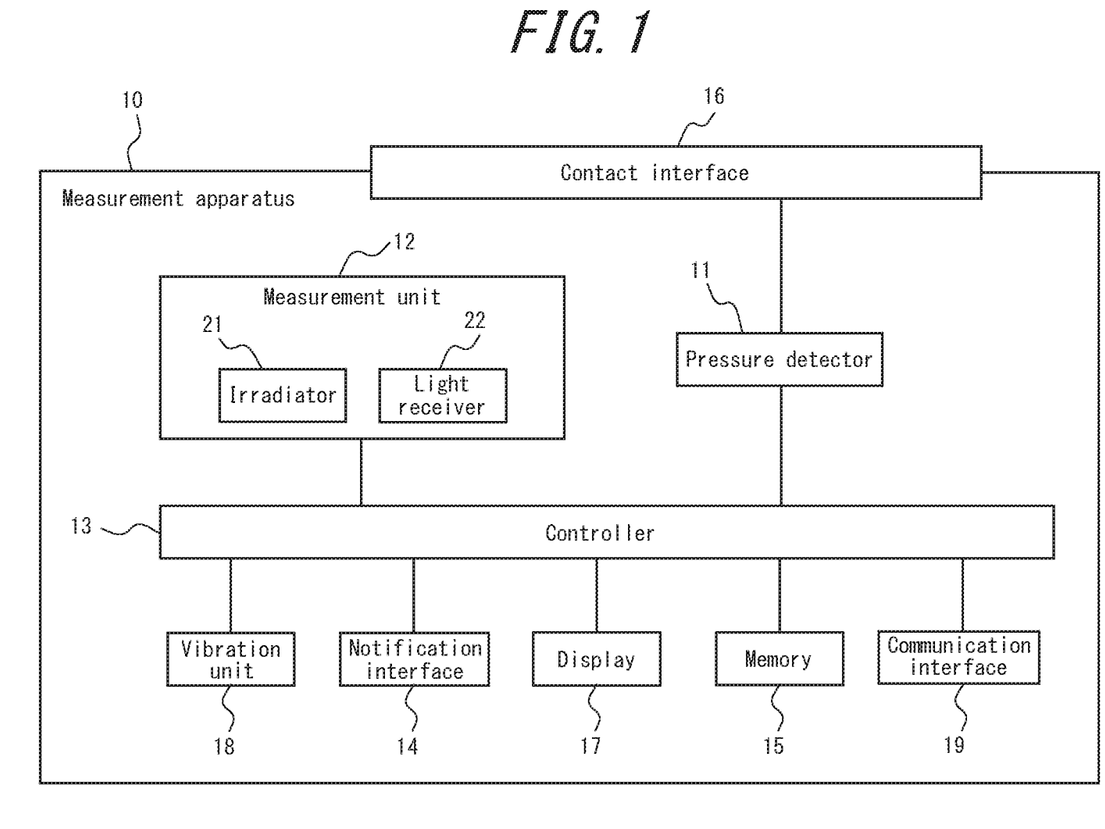
FIG. 1 is a block diagram schematically illustrating the structure of a measurement apparatus according to Embodiment 1.

FIG. 1 is a block diagram schematically illustrating the structure of a measurement apparatus according to Embodiment 1. As illustrated in FIG. 1, the measurement apparatus 10 includes a pressure detector 11, a measurement unit 12, a controller 13, a notification interface 14, a memory 15, a contact interface 16, a display 17, a vibration unit 18, and a communication interface 19.

Figure 2:
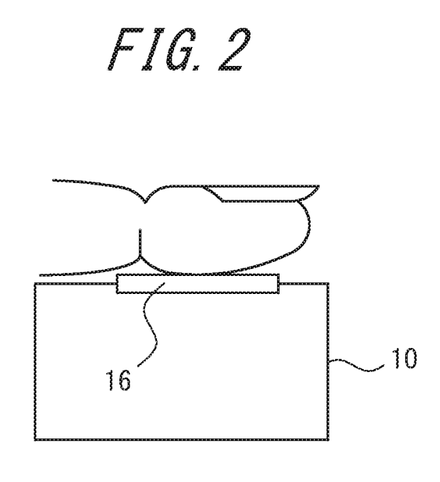
FIG. 2 illustrates an example of a usage state of the measurement apparatus.

The measurement apparatus 10 uses the measurement unit 12, which for example is configured by a biological sensor or the like, to acquire biological measurement output of a subject (user) that is in contact with the contact interface 16 and measures biological information based on the biological measurement output. FIG. 2 illustrates an example of a usage state of the measurement apparatus 10, illustrating a state in which the user is pressing the finger of a hand, which is a test site, against the measurement apparatus 10. The measurement apparatus 10 may be configured to acquire biological measurement output using the measurement unit 12 and to measure biological information while a finger is being pressed against the contact interface 16, as in FIG. 2. Measurement of the biological information by the measurement apparatus 10, however, is not limited to the configuration in this example.

With regard to the contact pressure with which the finger (test site) contacts the contact interface 16, there may be an appropriate pressure range suitable for acquisition when the measurement apparatus 10 acquires the biological measurement output in the measurement unit 12. In other words, when the contact pressure on the contact interface 16 is too strong or too weak, then acquisition of accurate biological measurement output might not be possible, for example because of the test site being affected by the pressure, or because of the effect of noise. If accurate biological measurement output cannot be acquired, it becomes difficult to measure highly accurate biological information.

The measurement apparatus 10 of this embodiment can detect the contact pressure of the test site contacting the contact interface 16 with the pressure detector 11. In this case, in the controller 13, the measurement apparatus 10 may measure the biological information based on the biological measurement output when the contact pressure is in a predetermined range. At this time, the measurement apparatus 10 provides notification, via the notification interface 14, of information related to the contact pressure. With this notification, the user can learn information related to contact pressure. For example, the user can learn whether the contact pressure is within a predetermined range, such as a suitable range that is appropriate for measuring the biological information, and whether the contact pressure is stronger or weaker than pressure in the predetermined range. Measurement of the biological information by the measurement apparatus 10, however, is not limited to such a configuration that detects contact pressure of the test site.

The biological information measured by the measurement apparatus 10 can be any biological information that can be measured using the measurement unit 12. As an example in this embodiment, the measurement apparatus 10 is described as measuring the amount of blood flow of a subject as the biological information.

The pressure detector 11 detects the contact pressure of the test site on the contact interface 16. The pressure detector 11 may, for example, be configured using a piezoelectric element. The pressure detector 11 is connected to the controller 13 and transmits the detected pressure signal to the controller 13.

The measurement unit 12 is configured by a biological sensor or the like, as described above, and acquires biological measurement output from the test site. When the measurement apparatus 10 measures the amount of blood flow, as in this embodiment, then the measurement unit 12 for example includes an irradiator 21 and a light receiver 22. The irradiator 21 irradiates measurement light onto the test site in contact with the contact interface 16. The irradiator 21 may, for example, be configured by a laser light source that irradiates, as measurement light, laser light with a wavelength that can detect a predetermined component included in blood. An example of such a laser light source is a Laser Diode (LD). As biological measurement output, the light receiver 22 receives scattered light (detected light) that is scattered from the test site by the irradiator 21 irradiating measurement light onto the test site. The light receiver 22 is configured by a photodiode (PD). The measurement unit 12 transmits a photoelectric conversion signal of the scattered light received by the light receiver 22 to the controller 13.

The measurement unit 12 may, for example, be activated when the contact pressure is within the above-described predetermined range. In order for the measurement apparatus 10 to measure the biological information based on the biological measurement output when the contact pressure is within the above-described predetermined range, it suffices for the measurement unit 12 to acquire the biological measurement output at least when the contact pressure is within the above-described predetermined range. By the measurement unit 12 activating when the contact pressure is within the above-described predetermined range, emission of laser light from the irradiator 21 and leakage of laser light to the surroundings can be prevented when acquisition of biological measurement output is unnecessary.

The controller 13 is a processor that, starting with the functional blocks of the measurement apparatus 10, controls and manages the measurement apparatus 10 overall. The controller 13 is configured using a processor such as a Central Processing Unit (CPU) that executes a program prescribing control procedures. Such a program may, for example, be stored in the memory 15, in an external storage medium, or the like.

The controller 13 judges whether the acquisition of the biological measurement output by the measurement unit 12 is complete. The controller 13 may, for example, judge that acquisition of the biological measurement output is complete once a predetermined length of time elapses after the measurement unit 12 starts to acquire the biological measurement output. The controller 13 may also, for example, judge that acquisition of the biological measurement output is complete once the measurement unit 12 has acquired sufficient biological measurement output to measure the biological information.

The controller 13 may measure the biological information based on the biological measurement output when the contact pressure on the contact interface 16 is in a predetermined range. The controller 13 may, for example, measure the amount of blood flow as biological information by using an algorithm, table, or the like that measures the amount of blood flow based on a change in the intensity of the scattered light received by the light receiver 22. In order to measure the biological information based on the biological measurement output when the contact pressure is in a predetermined range, the controller 13 can judge whether the contact pressure is in a predetermined range based on the contact pressure detected by the pressure detector 11.

A technique for the controller 13 to measure the amount of blood flow using the Doppler shift is now described. When measuring the amount of blood flow, the controller 13 irradiates laser light from the irradiator 21 onto body tissue and receives scattered light that is scattered from the body tissue with the light receiver 22. The controller 13 then calculates the amount of blood flow based on the measurement result of the received laser light.

In the body tissue, scattered light that is scattered from moving blood cells undergoes a frequency shift (Doppler shift), due to the Doppler effect, relative to the speed of travel of the blood cells within the blood. The controller 13 detects the beat signal due to interference between scattered light from still tissue and the scattered light from moving blood cells. This beat signal represents strength as a function of time. The controller 13 then turns the beat signal into a power spectrum that represents power as a function of frequency. In this power spectrum of the beat signal, the Doppler shift frequency is proportional to the speed of blood cells, and the power corresponds to the amount of blood cells. The controller 13 calculates the amount of blood flow by multiplying the power spectrum of the beat signal by the frequency and integrating.

The notification interface 14 notifies the user, who is a subject, of information such as information related to the contact pressure on the contact interface 16. The measurement apparatus 10 can measure the biological information based on the biological measurement output when the contact pressure is in a predetermined range. In other words, the contact pressure being in a predetermined range can be set as a condition for measuring the biological information. Therefore, by notifying the user of information related to the contact pressure, the notification interface 14 can encourage the user to adjust the contact pressure to be within a predetermined range.

In order to encourage the user to adjust the contact pressure to be within a predetermined range, the notification interface 14 may, as the information related to the contact pressure, notify the user of information regarding whether the contact pressure is within a predetermined range. This approach is more convenient for the user.

For example, the notification interface 14 can include a speaker and provide notification of information related to the contact pressure by outputting sound. The notification interface 14 can also, for example, provide notification of information related to the contact pressure by displaying an image on the display 17. The notification interface 14 may also provide notification of information related to the contact pressure by displaying characters on the display 17. The notification interface 14 can also, for example, include a light-emitting device and provide notification of information related to the contact pressure by light emission from the light-emitting device.

The notification interface 14 can also, for example, include a vibration unit, such as a vibrator or a piezoelectric element, and provide notification of information related to the contact pressure by the vibration of the vibration unit. When the notification interface 14 provides notification by vibration, however, the pressure of the test site preferably does not change due to the vibration.

Notification methods by the notification interface 14 based on output of sound, display of images, light emission, and output of vibration have been described, but a notification method by the notification interface 14 is not limited to the above-described notification methods. In the case of the contact pressure being outside of the allowable pressure range, the notification interface 14 may provide notification with different methods when the contact pressure is stronger than and weaker than the allowable pressure range. The notification interface 14 may also notify the user of the contact pressure with any combination of methods.

Furthermore, the notification interface 14 may provide notification of information related to the difference between the contact pressure and at least one of suitable pressure and allowable pressure.

In this way, the notification interface 14 can provide notification of information related to the difference between the contact pressure and at least one of suitable pressure and allowable pressure. As a result, the user can easily recognize how much to increase or decrease the pressure of the finger contacting the contact interface 16. Therefore, the user can easily adjust the contact pressure. With this sort of display, the user can also make adjustments to maintain the contact pressure within the range of suitable pressure or allowable pressure while confirming the notification of the notification interface 14.

The notification interface 14 can also provide the user with notification at the start and the end of acquisition of biological measurement output by the measurement unit 12. By being notified of the start of acquisition, the user can recognize the need to maintain the pressure state of the finger, and by being notified of the end of acquisition, the user can recognize that the finger can be released from the contact interface 16. The notification interface 14 may also provide notification of information related to the measurement result of biological information.

The memory 15 may be configured with a semiconductor memory or the like. The memory 15 stores a variety of information, programs for causing the measurement apparatus 10 to operate, and the like and also functions as a working memory. The memory 15 also stores information such as history data in which the biological information measured by the measurement apparatus 10 is associated with the contact pressure at the time the biological information was measured. When measuring the biological information, the controller 13 may measure the biological information by referring to history data based on the contact pressure detected by the pressure detector 11 and the biological measurement output measured by the measurement unit 12.

When the controller 13 thus measures the biological information by referring to history data, the measurement unit 12 for example acquires a predetermined number of biological measurement outputs during a predetermined time. The predetermined time and the predetermined number of biological measurement outputs may be set to any values. For example, the measurement unit 12 may acquire five biological measurement outputs by measuring once per second for five seconds.

As an example of a method of measuring other biological information by referring to the history data, the controller 13 may refer to the history data and determine weights in accordance with the measurement accuracy of biological information for each of the contact pressures of five biological measurement outputs. For example, the controller 13 can determine to apply high weighting to a biological measurement output related to contact pressure with high measurement accuracy. For the five biological measurement outputs, the controller 13 can then measure the biological information by calculating a weighted average that reflects the determined weights.

By thus measuring the biological information while taking into account history data stored in the memory 15, the controller 13 can improve the measurement accuracy of biological information.

The contact interface 16 is a portion that contacts the test site, such as a finger, in order for the user to measure biological information. The contact interface 16 may, for example, be configured by a plate-shaped member. The contact interface 16 may also be configured by a member that is transparent at least with respect to the measurement light and the detected light. The pressure detector 11 detects pressure on the contact interface 16 when a finger or the like contacts the contact interface 16 and transmits the detected contact pressure to the controller 13.

The display 17 is a display device for example configured by a well-known display. The display 17 for example displays the biological information measured by the controller 13. The display 17 can be configured by a variety of display devices, such as a liquid crystal display (LCD), an organic EL display, or the like.

By generating vibration, the vibration unit 18 can vibrate a portion of the measurement apparatus 10, such as the contact interface 16, and provide a variety of tactile sensations to the subject (user). The vibration unit 18 can generate a variety of vibrations with predetermined driving signals supplied by the controller 13. In particular, when the electronic device provided with the measurement apparatus 10 is implemented as a communication device, such as a mobile phone or smartphone, the vibration unit 18 provides a vibration function. As a result, at the time of an incoming phone call, receipt of an e-mail, or the like, a communication device provided with the measurement apparatus 10 can notify the user of the incoming phone call, the received e-mail, or the like with the vibration function instead of, or along with, sound generation.

The vibration unit 18 may be configured using any number of piezoelectric vibrators, using a transparent piezoelectric element on the entire surface of the touch sensor, or by causing an eccentric motor to rotate once per period of a drive signal, as long as the eccentric motor can express vibration that presents a tactile sensation. For example, as the method for generating vibration, the vibration unit 18 may use an Eccentric Rotating Mass (ERM) method that produces rotation with a motor that has offset mass on the shaft. Other methods for the vibration unit 18 to generate vibration include a Linear Resonant Actuator (LRA) method that configures an actuator in the manner of a linear motor and induces resonance. Furthermore, as the method for generating vibration, the vibration unit 18 may adopt a piezo actuator that uses a "piezoelectric element," which is a material that changes shape in accordance with voltage being on/off. The vibration unit 18 according to this embodiment may have any configuration that generates suitable vibration.

By transmitting and receiving signals to and from the exterior of the measurement apparatus 10 over a wired or wireless connection, the communication interface 19 exchanges a variety of information. In other words, the communication interface 19 communicates over a wired or wireless connection. In particular, in a communication device such as a mobile phone or smartphone provided with the measurement apparatus 10, the communication interface 19 places and receives phone calls, transmits and receives e-mail, and the like by communicating with a base station.

In this embodiment, the communication interface 19 may be configured using any of a variety of wireless communication means or the like. Therefore, a detailed explanation is omitted.

In a communication device such as a mobile phone or smartphone provided with the measurement apparatus 10, upon the communication interface 19 receiving a phone call transmitted by a base station, the controller 13 normally executes processing related to phone call reception with high priority. Similarly, in a communication device such as a mobile phone or smartphone provided with the measurement apparatus 10, upon the communication interface 19 receiving an e-mail transmitted by a base station, the controller 13 normally executes processing related to e-mail reception with high priority.

Next, operations of the measurement apparatus 10 according to this embodiment are described.

It is assumed below that the measurement apparatus 10 according to this embodiment is provided in a communication device such as a mobile phone or smartphone. Therefore, when the user of the measurement apparatus 10 is measuring biological information using the measurement apparatus 10, there is a risk that the biological information will not be measured correctly if, for example, there is an incoming phone call, or an e-mail is received. Therefore, in this embodiment, the appropriate action to be taken by the measurement apparatus 10 is prescribed for the case of processing with high priority, such as an incoming phone call, reception of e-mail, or the like occurring so as to interrupt processing on the measurement apparatus 10.

Figure 3:
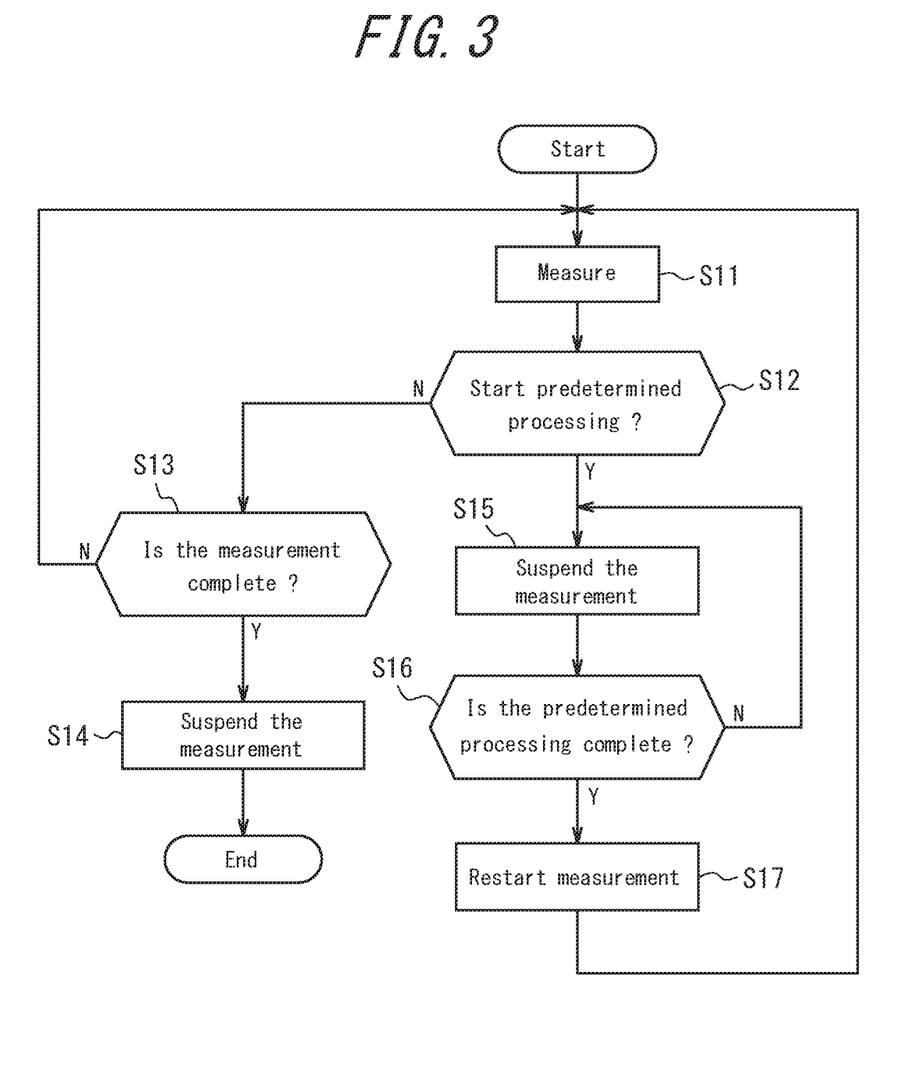
FIG. 3 is a flowchart illustrating operations of a measurement apparatus according to Embodiment 1.

FIG. 3 is a flowchart illustrating an example of operations of the measurement apparatus 10 according to this embodiment. In the following explanation of FIG. 3, it is assumed that while measuring biological information with the measurement apparatus 10, predetermined processing such as processing related to a phone call begins in the electronic device that is provided with the measurement apparatus 10.

At the time of measuring biological information with the measurement apparatus 10, for example when measuring the amount of blood flow, the user first contacts the finger, which is a test site, to the contact interface 16. In such a state, the controller 13 starts the processing illustrated in FIG. 3, for example with input from the subject (user) as a trigger. Once the processing in FIG. 3 starts, the controller 13 performs control so as to start measurement of biological information by the measurement unit 12 (step S11).

Once measurement of biological information starts in step S11, the controller 13 determines whether to start predetermined processing in response to the occurrence of processing prescribed in advance as high priority, such as an incoming phone call, receipt of an e-mail, or the like (step S12). The determination made in step S12 as to whether processing has occurred is not limited to processing such as an incoming phone call or receipt of e-mail. The determination made in step S12 as to whether processing has occurred may be for processing that is prescribed in advance as being high priority in terms of functions of the electronic device in which the measurement apparatus 10 is mounted.

Here, "predetermined processing" is envisioned as processing that, for example, launches phone call application software (an application) in response to an incoming phone call. The predetermined processing may also be processing that, in response to an incoming phone call, switches a telephone application from running in the background to running in the foreground. The predetermined processing may also include processing related to an operation executed based on the running telephone application. Furthermore, the predetermined processing is, for example, envisioned as processing that launches an e-mail application in response to reception of e-mail. The predetermined processing may also be processing that, in response to receipt of e-mail, switches an e-mail application from running in the background to running in the foreground. The predetermined processing may also include processing related to an operation executed based on the running e-mail application.

When the electronic device provided with the measurement apparatus 10 of this embodiment is configured as a communication device, the above-described "predetermined processing" is mainly processing related to communication between the communication interface 19 and an external source. In this embodiment, processing related to communication between the communication interface 19 and an external source may, for example, be processing related to an incoming phone call, processing related to receiving an e-mail, or the like. Therefore, in this embodiment, the predetermined processing may be processing related to control of the communication interface 19, in particular processing related to control when the communication interface 19 executes incoming communication processing.

When determining not to start predetermined processing in step S12 (i.e. when there is no incoming phone call, no receipt of e-mail, and the like), the controller 13 determines whether the measurement started in step S11 is complete (step S13). Once the measurement in step S13 is complete, the controller 13 performs control to suspend measurement of biological information by the measurement unit 12 (step S14) and terminates operations according to this embodiment. If the measurement is not complete in step S13, the controller 13 returns to step S11 and continues measurement of biological information by the measurement unit 12.

On the other hand, when starting predetermined processing in step S12 (i.e. when there is an incoming phone call, receipt of e-mail, or the like), the controller 13 performs control to suspend measurement of biological information by the measurement unit 12 (step S15). Upon suspending measurement in step S15, the controller 13 determines whether the predetermined processing started in step S12 has finished (step S16) and performs control to suspend measurement of biological information by the measurement unit 12 until the predetermined processing finishes (step S15). Here, for example in the case of a telephone application, stating that the predetermined processing finishes may be envisioned to refer to the telephone application being terminated upon the telephone call ending. For example in the case of an e-mail application, stating that the predetermined processing finishes may be envisioned to refer to the e-mail application being terminated based on user operation.

Once the predetermined processing in step S16 has finished, the controller 13 performs control to restart the measurement that was suspended in step S15 (step S17). When restarting the suspended measurement in step S17, the controller 13 may request that the user perform an operation to restart measurement and then perform control to restart measurement with user input as a trigger. In step S17, the controller 13 may for example display an indication that measurement is restarting, for example on the display 17, and then automatically restart measurement. After restarting measurement in step S17, the controller 13 executes the processing from step S11 onward.

In this way, in the measurement apparatus 10 according to this embodiment, the controller 13 performs control to suspend measurement by the measurement unit 12 when starting predetermined processing during measurement by the measurement unit 12. After starting predetermined processing during measurement by the measurement unit 12, the controller 13 may perform control to restart measurement by the measurement unit 12 when the predetermined processing has finished.

When mounted in a mobile phone, smartphone, or the like, the measurement apparatus 10 according to this embodiment suspends measurement by the measurement unit 12 when an incoming call, receipt of e-mail, or the like occurs so as to interrupt during measurement of biological information. Therefore, according to this embodiment, even if an incoming call, receipt of e-mail, or the like occurs so as to interrupt during measurement of biological information, the measurement accuracy can be prevented from worsening as a result, thereby allowing improvement in the reliability of measurement. Furthermore, according to this embodiment, when an incoming call, receipt of e-mail, or the like occurs so as to interrupt, measurement by the measurement unit 12 is suspended. Therefore, the power that would have subsequently been consumed by the measurement unit 12 can be prevented from being wasted.

Embodiment 2

The following describes a measurement apparatus according to Embodiment 2. In Embodiment 1, the reliability of measurements can be improved as described above, but measurement is discontinued when an incoming call, receipt of e-mail, or the like occurs so as to interrupt. To address this issue, in Embodiment 2, measurement is not discontinued even when an incoming call, receipt of e-mail, or the like occurs so as to interrupt during measurement of biological information.

The measurement apparatus according to Embodiment 2 can be implemented with the same structure as that of the measurement apparatus 10 according to Embodiment 1, while changing the processing pertaining to operations. Accordingly, explanation that is similar as for Embodiment 1 is appropriately omitted, with the explanation focusing on the particular content of Embodiment 2 that differs from Embodiment 1.

When the user of the measurement apparatus 10 is measuring biological information, if for example an event such as an incoming phone call or receipt of an e-mail occurs, and vibration is generated by the vibration function to cause the user to recognize the event, then there is a risk that the biological information will not be measured correctly. For example, upon vibration being generated during measurement of biological information, as a result of vibration of the mobile phone, smartphone, or the like that is provided with the measurement apparatus 10, there is a risk that the test site, such as the subject's (user's) fingertip, will not be maintained appropriately in a state of contact with the contact interface 16. Also, upon vibration of the measurement apparatus 10 during measurement of the biological information, the subject (user) may, for example, be surprised by the sudden vibration, and a variety of conditions may change, such as the subject's heart rate. Hence, there is a risk of change in the measured biological information. Therefore, in this embodiment as well, the appropriate action to be taken by the measurement apparatus 10 is prescribed for the case of processing with high priority, such as reception of a phone call or an e-mail, occurring so as to interrupt processing on the measurement apparatus 10.

Figure 4:
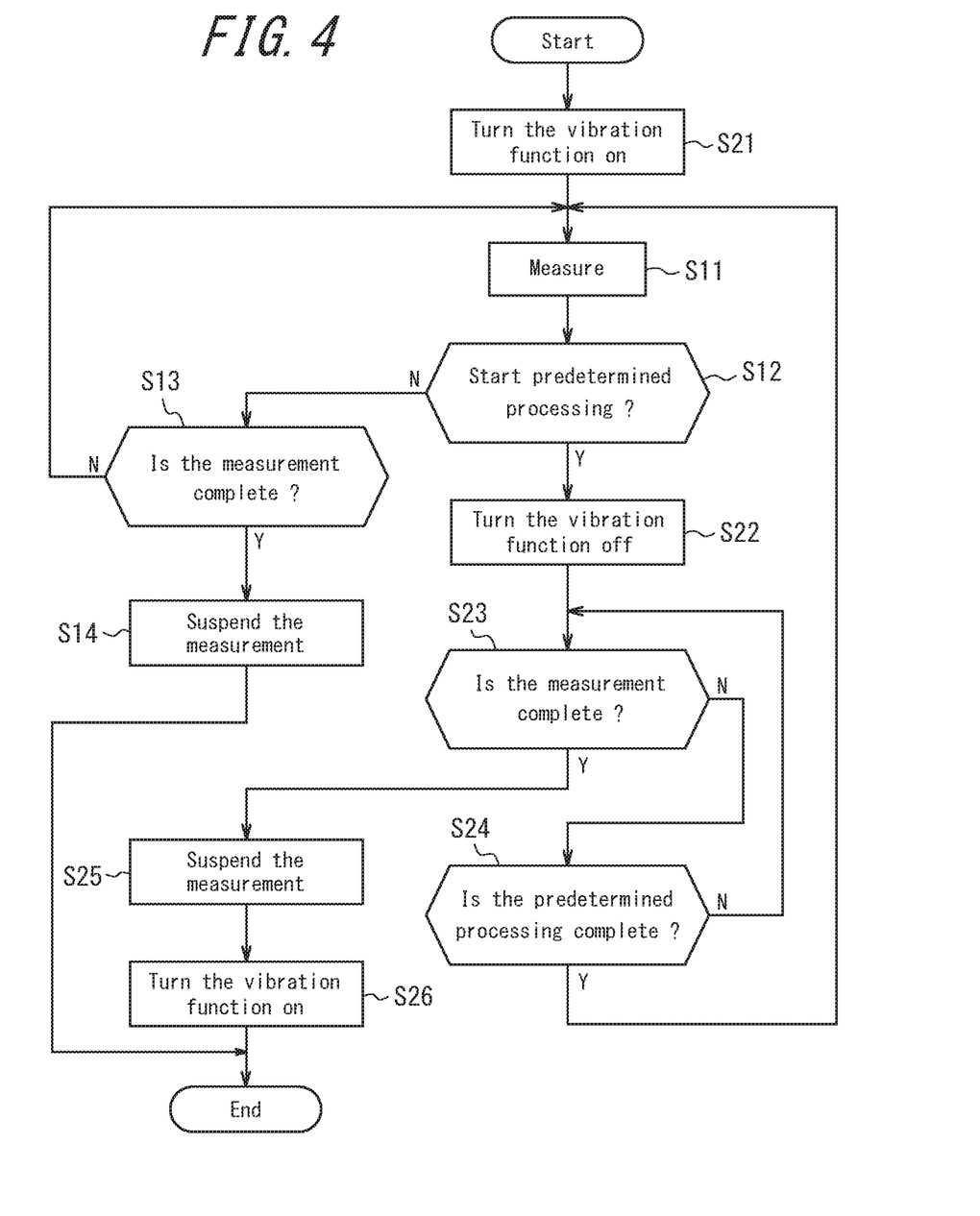
FIG. 4 is a flowchart illustrating operations of a measurement apparatus according to Embodiment 2.

FIG. 4 is a flowchart illustrating an example of operations of the measurement apparatus 10 according to this embodiment. In the following explanation of FIG. 4, it is assumed that while measuring biological information with the measurement apparatus 10, predetermined processing such as processing related to a phone call begins in the electronic device that is provided with the measurement apparatus 10.

As illustrated in FIG. 4, upon the operations of this embodiment starting, the controller 13 first performs control so that the function by which the vibration unit 18 generates vibration (vibration function) is on (step S21). In this embodiment, the controller 13 may turn the vibration function on before the start of operations illustrated in FIG. 4. In either case, in this embodiment, it is assumed that the vibration function is on at the point at which measurement of biological information starts.

Once the vibration function is on in step S21, the controller 13 performs control to start measurement of biological information by the measurement unit 12, for example with input by the subject (user) as a trigger (step S11). In this embodiment as well, at the time of measuring biological information with the measurement apparatus 10, for example when measuring the amount of blood flow, the user contacts the finger, which is a test site, to the contact interface 16.

Once measurement of biological information starts in step S11, the controller 13 determines whether to start predetermined processing in response to the occurrence of processing prescribed in advance as high priority, such as an incoming phone call, receipt of an e-mail, or the like (step S12). Here, the predetermined processing may be similar processing to that described in Embodiment 1. When determining not to start predetermined processing in step S12, the controller 13 determines whether the measurement started in step S11 is complete (step S13). Once the measurement in step S13 is complete, the controller 13 performs control to suspend measurement of biological information by the measurement unit 12 (step S14) and terminates operations according to this embodiment. If the measurement is not complete in step S13, the controller 13 returns to step S11 and continues measurement of biological information by the measurement unit 12.

On the other hand, when starting predetermined processing in step S12 (i.e. when there is an incoming phone call, receipt of e-mail, or the like), the controller 13 performs control so that the function by which the vibration unit 18 generates vibration, i.e. the vibration function, is turned off (step S22). Once the vibration function is turned off in step S22, the controller 13 continues measurement of biological information by the measurement unit 12 and judges whether the measurement begun in step S11 is complete (step S23).

When the measurement is not yet complete in step S23, the controller 13 determines whether the predetermined processing started in step S12 has finished (step S24). Here, stating that the predetermined processing has finished may refer to similar processing as that described in Embodiment 1. When the predetermined processing is not complete in step S24, the controller 13 performs control to continue measurement of biological information by the measurement unit 12 until the predetermined processing finishes (step S23). When the predetermined processing has finished in step S24, the controller 13 returns to step S11 and continues measurement of biological information by the measurement unit 12.

On the other hand, when the measurement is complete in step S23, the controller 13 performs control to suspend measurement of biological information by the measurement unit 12 (step S25), turns the vibration function on (step S26), and terminates operations according to this embodiment.

In this way, in the measurement apparatus 10 according to this embodiment, when starting predetermined processing during measurement by the measurement unit 12, the controller 13 performs control so that vibration is not generated by the vibration unit 18 and then continues measurement by the measurement unit 12. After starting predetermined processing during measurement by the measurement unit 12, the controller 13 may perform control to allow the vibration unit 18 to generate vibration at the time the predetermined processing finishes.

When mounted in a mobile phone, smartphone, or the like, the measurement apparatus 10 according to this embodiment performs control so that the vibration unit 18 does not vibrate even when an incoming call, receipt of e-mail, or the like occurs so as to interrupt during measurement of biological information. Therefore, according to this embodiment, even if an incoming call, receipt of e-mail, or the like occurs so as to interrupt during measurement of biological information, the measurement accuracy can be prevented from worsening due to resulting vibration, thereby allowing improvement in the reliability of measurement.

As a modification to Embodiment 2, when starting predetermined processing during measurement by the measurement unit 12, in addition to or instead of control so that the vibration unit 18 does not generate vibration, control may be performed so that sound is not emitted from the notification interface 14. Upon output of sound by the notification interface 14 of the measurement apparatus 10 during measurement of the biological information, the subject (user) may, for example, be surprised by the sudden sound (such as a loud sound), and a variety of conditions may change, such as the subject's heart rate. Hence, there is a risk of change in the measured biological information. Accordingly, such an inconvenience can be avoided by performing control, when starting predetermined processing during measurement by the measurement unit 12, so that sound is not emitted from the notification interface 14. Even when emission of both vibration and sound by the measurement apparatus 10 during measurement of the biological information is suppressed in this way, if an incoming call, reception of e-mail, or the like occurs, the subject (user) can learn of the incoming call, received e-mail, or the like by the display on the display 17.

Embodiment 3

The following describes a measurement apparatus according to Embodiment 3. In Embodiment 3, as in Embodiment 1, when an incoming call, receipt of e-mail, or the like occurs so as to interrupt, measurement of biological information is discontinued. In Embodiment 3, however, it is determined whether to output the result measured up until that time or to use the result in the next measurement in accordance with the conditions of measurement made up until that time.

The measurement apparatus according to Embodiment 3 can be implemented with the same structure as that of the measurement apparatus 10 according to Embodiment 1 or 2, while changing the processing pertaining to operations. Accordingly, explanation that is similar as for Embodiment 1 or 2 is appropriately omitted, with the explanation focusing on the particular content of Embodiment 3 that differs from Embodiments 1 and 2.

Figure 5:
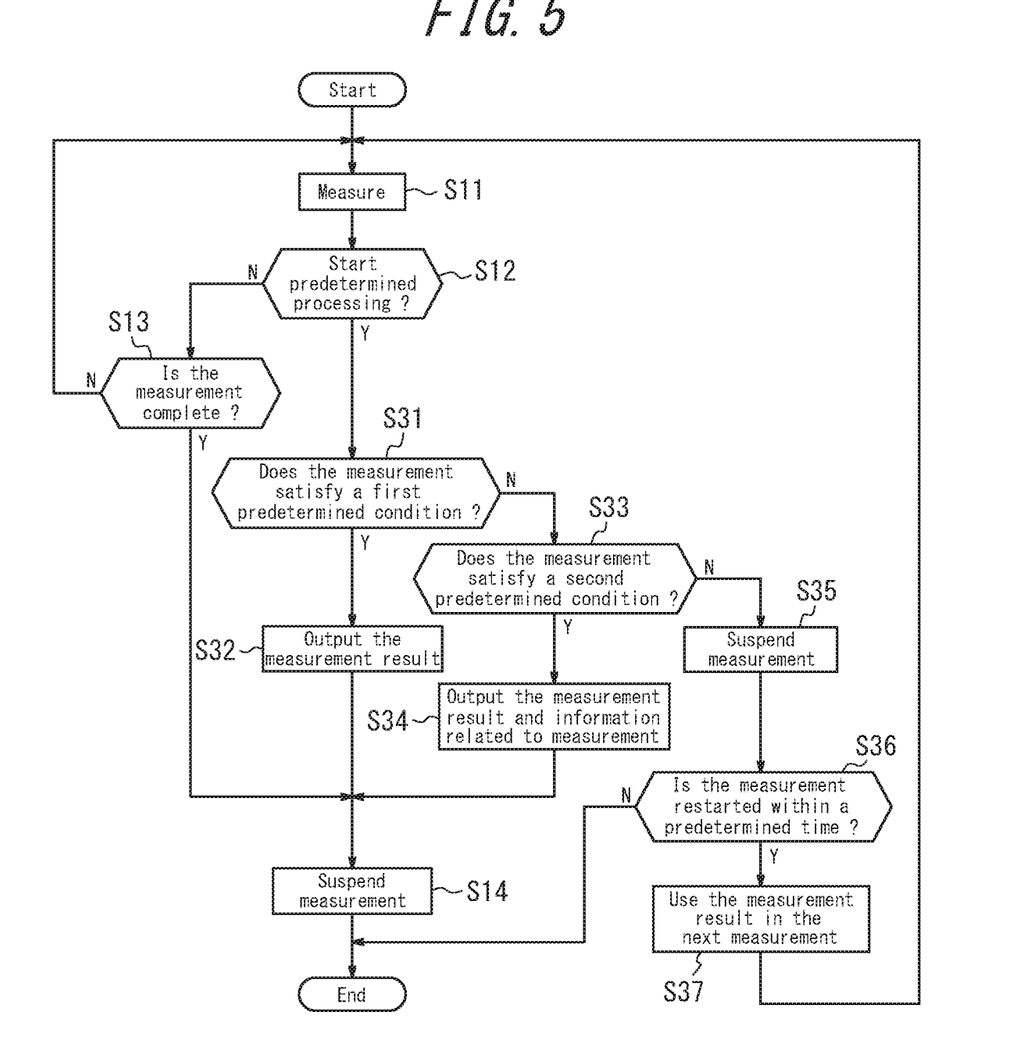
FIG. 5 is a flowchart illustrating operations of a measurement apparatus according to Embodiment 3.

FIG. 5 is a flowchart illustrating an example of operations of the measurement apparatus 10 according to this embodiment. In the following explanation of FIG. 5, it is assumed that while measuring biological information with the measurement apparatus 10, predetermined processing such as processing related to a phone call begins in the electronic device that is provided with the measurement apparatus 10.

In this embodiment, at the time of measuring biological information with the measurement apparatus 10, for example when measuring the amount of blood flow, the user first contacts the finger, which is a test site, to the contact interface 16. In such a state, the controller 13 starts the processing illustrated in FIG. 5, for example with input from the subject (user) as a trigger. Once the processing in FIG. 5 starts, the controller 13 performs control so as to start measurement of biological information by the measurement unit 12 (step S11).

Once measurement of biological information starts in step S11, the controller 13 determines whether to start predetermined processing in response to the occurrence of processing prescribed in advance as high priority, such as an incoming phone call, receipt of an e-mail, or the like (step S12). Here, the predetermined processing may be similar processing to that described in Embodiment 1. When determining not to start predetermined processing in step S12, the controller 13 determines whether the measurement started in step S11 is complete (step S13). Once the measurement in step S13 is complete, the controller 13 performs control to suspend measurement of biological information by the measurement unit 12 (step S14) and terminates operations according to this embodiment. If the measurement is not complete in step S13, the controller 13 returns to step S11 and continues measurement of biological information by the measurement unit 12.

On the other hand, when starting predetermined processing in step S12 (i.e. when there is an incoming phone call, receipt of e-mail, or the like), the controller 13 determines whether the measurement of biological information by the measurement unit 12 at that point in time satisfies a first predetermined condition (step S31). The first predetermined condition in step S31 may, for example, be that measurement of biological information by the measurement unit 12 at that point in time is at least 80% complete. In other words, this means that if the amount of data acquired is 100% when measurement of biological information by the measurement unit 12 is completed normally, at least 80% of the data has been acquired at that point in time.

When measurement in step S31 satisfies the first predetermined condition, the controller 13 determines that the majority of measurement is complete and outputs the result of measurement, for example to the display 17 (step S32). At this time, along with the result of measurement, the controller 13 may for example also output information indicating that since the majority of measurement was complete, the measurement result has relatively high reliability. Once the measurement result is output in step S32, the controller 13 performs control to suspend measurement of biological information by the measurement unit 12 (step S14) and terminates operations according to this embodiment.

On the other hand, when the measurement does not satisfy the first predetermined condition in step S31, the controller 13 determines whether the measurement of biological information by the measurement unit 12 at that point in time satisfies a second predetermined condition (step S33). The second predetermined condition in step S33 may, for example, be that measurement of biological information by the measurement unit 12 at that point in time is at least 50% complete. In other words, this means that if the amount of data acquired is 100% when measurement of biological information by the measurement unit 12 is completed normally, at least 50% of the data has been acquired at that point in time.

When measurement in step S33 satisfies the second predetermined condition, the controller 13 determines that measurement is partially complete and outputs the result of measurement, for example to the display 17 (step S34). In step S34, along with the result of measurement, the controller 13 for example also outputs information indicating that since measurement is only partially complete, the measurement result has relatively low reliability. Once the measurement result is output in step S34, the controller 13 performs control to suspend measurement of biological information by the measurement unit 12 (step S14) and terminates operations according to this embodiment.

On the other hand, when the measurement does not satisfy the second predetermined condition in step S33, the controller 13 performs control to suspend measurement of biological information by the measurement unit 12 (step S35). Once measurement is suspended in step S35, the controller 13 determines whether measurement of biological information by the measurement unit 12 was restarted within a predetermined time, for example with input by the subject (user) as a trigger (step S36). The predetermined time until measurement of biological information is made again refers to an appropriate time, such as several seconds to several tens of seconds, in which the subject's (user's) biological information is thought not to change greatly and may be set in advance taking various conditions into consideration. In step S36, when determining that measurement of biological information was not restarted within a predetermined time, the controller 13 terminates operations according to this embodiment.

Conversely, when determining that measurement of biological information was restarted within a predetermined time in step S36, the controller 13 restarts measurement of biological information while using the result measured by the measurement unit 12 up until that time (step S37).

In this way, in the measurement apparatus 10 according to this embodiment, when starting predetermined processing during measurement by the measurement unit 12, the controller 13 performs control to determine whether to output the measurement result in accordance with measurement made by the measurement unit 12 up until the start of the predetermined processing.

The controller 13 may perform control to output the measurement result when the measurement made by the measurement unit 12 up until the start of the predetermined processing satisfies a predetermined condition, such as being at least 80% complete. When the measurement made by the measurement unit 12 up until the start of the predetermined processing satisfies a predetermined condition, such as being at least 50% complete, the controller 13 also may perform control to output the measurement result along with information related to the measurement, such as an indication that the reliability of the measurement is low.

When the measurement made by the measurement unit 12 up until the start of the predetermined processing does not satisfy a predetermined condition, the controller 13 may perform control to use the measurement result in the next measurement by the measurement unit 12. In this case, the controller 13 may perform control to use the measurement result in the next measurement by the measurement unit 12 if the next measurement by the measurement unit 12 is made within a predetermined time.

When the measurement apparatus 10 according to this embodiment is mounted in a mobile phone, smartphone, or the like, if an incoming call, receipt of e-mail, or the like occurs so as to interrupt during measurement of biological information, the measurement apparatus 10 processes the measurement result in accordance with measurement up until that point. Therefore, according to this embodiment, when an incoming call, receipt of e-mail, or the like occurs so as to interrupt during measurement of biological information, if the measurement has progressed to some degree, the subject (user) is notified of the measurement result up until that point and of the reliability of the measurement. Accordingly, even if the measurement was not completed normally, the subject (user) can learn the measurement result along with information regarding the reliability thereof.

Furthermore, according to this embodiment, when an incoming call, receipt of e-mail, or the like occurs so as to interrupt during measurement of biological information, if the measurement has not progressed to some degree, the measurement result up until that point is used in the next measurement made within a predetermined time. Accordingly, even if the subject (user) cannot obtain the current measurement result, the time required for the next measurement can be shortened.

This disclosure is not limited to the above embodiments, and a variety of modifications and changes are possible. For example, the functions and the like included in the various components and steps may be reordered in any logically consistent way. Furthermore, components or steps may be combined into one or divided.

Figure 6A:
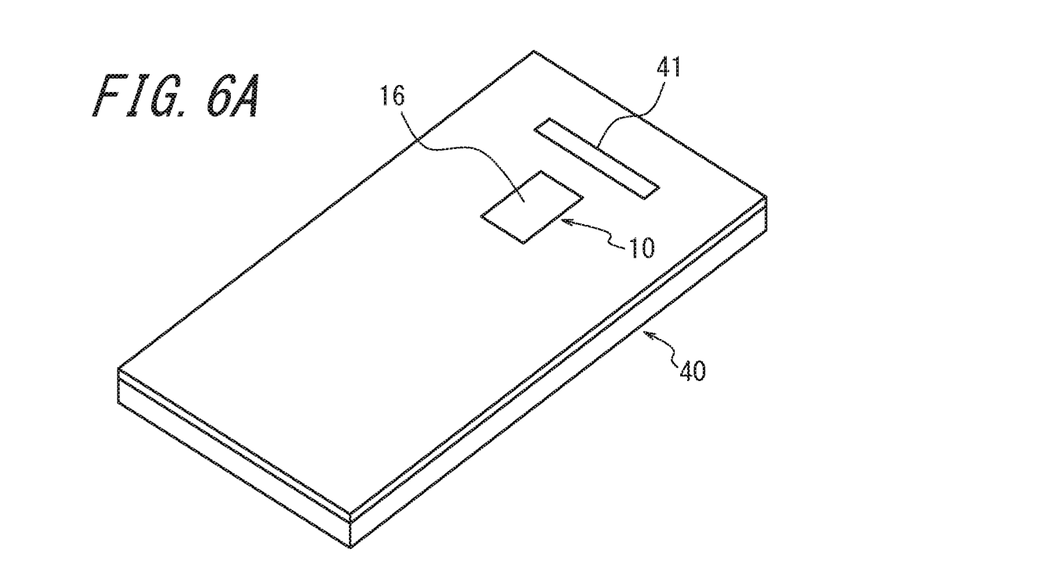
FIGS. 6A and 6B illustrate an example of a mobile phone in which the measurement apparatus of FIG. 1 is mounted.
Figure 6B:
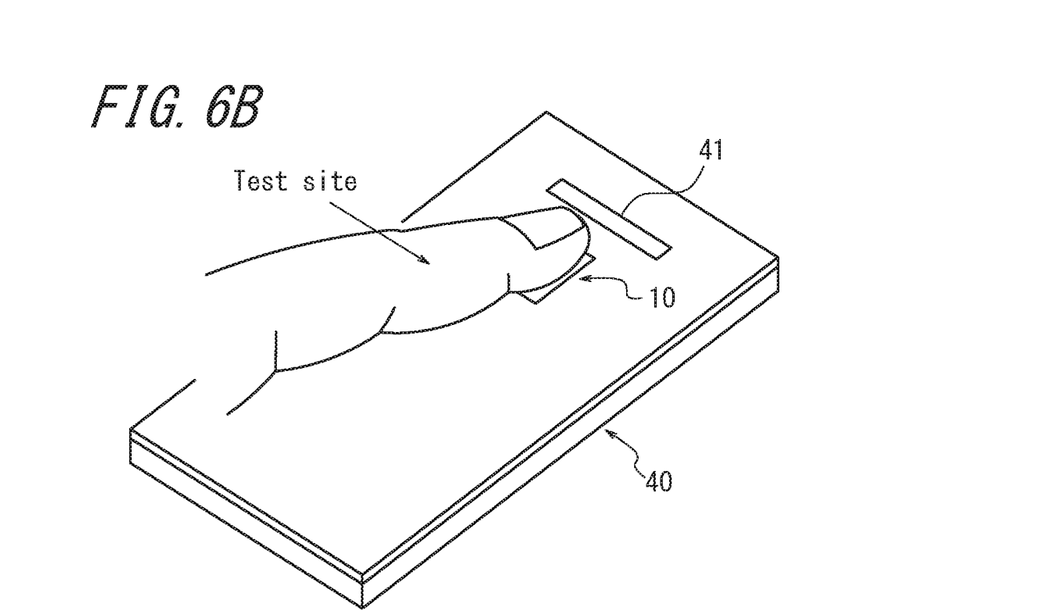

For example, the measurement apparatus 10 according to the above embodiments may be mounted in a variety of electronic devices. FIGS. 6A and 6B illustrate an example of a mobile phone in which the measurement apparatus 10 of FIG. 1 is mounted. In FIGS. 6A and 6B, a mobile phone is illustrated as an example of an electronic device in which the measurement apparatus 10 is mounted, but the electronic device in which the measurement apparatus 10 is mounted may be any of a variety of communication devices, such as a smartphone. As illustrated in FIG. 6A, the mobile phone 40 is provided with the measurement apparatus 10 on the back side thereof. The mobile phone 40 illustrated as an example in FIG. 6A is also provided with a back face display 41 on the back side thereof. The back face display 41 for example displays information related to contact pressure as an indicator. In this way, when the measurement apparatus 10 is mounted in an electronic device, the notification interface 14 may provide notification of information, from the electronic device, related to the contact pressure. In other words, FIGS. 6A and 6B illustrate an example of the notification interface 14 being configured as the back face display 41.

In FIGS. 6A and 6B, the display 17 may be configured as the back face display 41. For example, in Embodiment 2, when generation of vibration and sound by the measurement apparatus 10 are both suppressed during measurement of the biological information, then notification of an incoming call, receipt of e-mail, or the like may be provided by display on the back face display 41. In Embodiment 3, for example, the back face display 41 may display the measurement result and information related to the reliability of measurement that are output in step S32 or step S34.

FIG. 6B illustrates an example of the user using the mobile phone 40 provided with the measurement apparatus 10 to measure biological information. The user causes the measurement apparatus 10 to measure the biological information by contacting a finger to the contact interface 16. When measuring the biological information, the notification interface 14 may display information related to the contact pressure or the like on the back face display 41 as an indicator. The display of information related to the contact pressure is not limited to being performed on the back face display 41. For example, the notification interface 14 may display information related to the contact pressure by outputting sound from a speaker provided in the mobile phone 40, by causing a light-emitting device provided in the mobile phone 40 to emit light, or by causing a vibration unit provided in the mobile phone 40 to vibrate.

When measuring the biological information using the mobile phone 40 provided with the measurement apparatus 10, the measurement apparatus 10 may begin measurement of biological information by the user using the mobile phone 40 to launch an application exclusively for measuring biological information. The measurement apparatus 10 may also begin measurement of biological information automatically upon detecting contact pressure on the contact interface 16. In this case, the user can start measurement of biological information by contacting the finger to the contact interface 16, without launching an application.

When the user measures biological information using the mobile phone 40 provided with the measurement apparatus 10, the measurement apparatus 10 may notify the user of the measurement result with a variety of methods. For example, based on the measured value of the amount of blood flow, the measurement apparatus 10 may display, on a display provided in the mobile phone 40, an indication of whether the blood flow is "thin" or "thick" using a predetermined threshold as a standard. Based on the measured value of the amount of blood flow, the measurement apparatus 10 may, for example, reproduce different sounds using a predetermined threshold as a standard. Based on the measured value of the amount of blood flow, the measurement apparatus 10 may, for example, change the operability of the mobile phone 40 using a predetermined threshold as a standard. In this case, the user can learn the measurement result from the operability when operating the mobile phone 40.

When measuring the biological information, the measurement apparatus 10 may, for example, be configured to provide notification only indicating that measurement is complete. The measurement apparatus 10 may provide such notification by, for example, causing the vibration unit of the mobile phone 40 to vibrate. In this case, when the user wants to know the measurement result, the user can operate the mobile phone 40 to display the result on the mobile phone 40.

For example, the arrangement of the measurement apparatus 10 in the mobile phone 40 is not limited to the examples illustrated in FIGS. 6A and 6B. The measurement apparatus 10 may, for example, be disposed in a different part of the back face of the mobile phone 40 or may be disposed on the front face, side face, or the like of the mobile phone 40.

The electronic device in which the measurement apparatus 10 is mounted is not limited to the mobile phone 40. The measurement apparatus 10 may be mounted in any type of electronic device, such as a portable music player, a laptop computer, a wristwatch, a tablet, a game device, or the like.

The above embodiments may be implemented not only as the measurement apparatus 10 or an electronic device provided with the measurement apparatus 10, but also as methods for performing measurement on such an apparatus or device.

Although the disclosure is based on some embodiments and the accompanying drawings, it is to be noted that various changes and modifications will be apparent to those skilled in the art based on this disclosure. Therefore, such changes and modifications may be to be understood as included within the scope of this disclosure. For example, in some functions and structural components and the like of some embodiments may be reordered in any logically consistent way. Furthermore, the functions and the structural components may be combined into some embodiments or divided from an embodiment.

The invention claimed is:

1. A measurement apparatus comprising:
 a measurement unit configured to measure biological information;
 a communication interface; and
 a controller configured to
  start a measurement of the biological information,
  start a predetermined processing related to control of the communication interface, the predetermined processing interrupting the measurement,
  determine whether to output, as a result to a user, a partial result that is an output of the measurement from the start of the measurement up until the start of the predetermined processing, based on the partial result, and
  perform control to output the result when the partial result satisfies a first condition that is related to a completion rate of a measurement made by the measurement unit.

2. The measurement apparatus of claim 1, wherein
the controller performs control to output the result when the partial result satisfies a second condition, and the second condition is related to a completion rate of a measurement made by the measurement unit and is different from the first condition.

3. The measurement apparatus of claim 2, wherein
the controller performs control to use the result of the measurement in a next measurement by the measurement unit when the measurement made by the measurement unit up until the predetermined processing starts does not satisfy a second condition.

4. The measurement apparatus of claim 3, wherein
when the measurement made by the measurement unit up until the predetermined processing starts does not satisfy a second condition, the controller performs control to use the result of the measurement in the next measurement by the measurement unit upon the next measurement by the measurement unit being made within a predetermined time.

5. The measurement apparatus of claim 1, wherein
the predetermined processing is processing related to control when the communication interface executes incoming communication processing.

6. An electronic device comprising the measurement apparatus of claim 1.

* * * * *